United States Patent [19]

Lacy et al.

[11] Patent Number: 5,525,592
[45] Date of Patent: Jun. 11, 1996

[54] ALKALINE GLAND FLUID PROTEINS AND METHODS OF ENHANCING AND INHIBITING SPERM MOTILITY

[75] Inventors: Eric R. Lacy, 80 Vanderhorst St., Charleston, S.C. 29403; Subbi Mathur, Charleston, S.C.

[73] Assignee: Eric R. Lacy, Charleston, S.C.

[21] Appl. No.: 160,025

[22] Filed: Nov. 30, 1993

[51] Int. Cl.⁶ .......................... A61K 38/04; A61K 38/16; A01N 1/02; C07K 14/435
[52] U.S. Cl. .......................... 514/21; 514/12; 514/14; 435/2; 530/300; 530/324; 530/326; 530/327; 530/344; 530/350; 530/412
[58] Field of Search .................. 514/12, 14, 21, 514/841, 843, 967; 436/906; 435/806, 2; 424/422, 430, 433, 548, DIG. 14; 530/300, 324, 344, 326, 412, 327, 350, 857

[56] References Cited

U.S. PATENT DOCUMENTS 4,267,268  5/1981  Nelson, Jr. .......................... 435/2

OTHER PUBLICATIONS

Grabowski et al., "Ion Transport & Fluid Alkalinization of the Alkaline Gland of the Atlantic Stingray" FASEB J. 6(4) A1458, Abstract 3024, 1991.
Winston and Handyside Science 260:932–936, 1993.
Yovich et al., Fertility and Sterility 53(4):715–722, 1990.
Maren et al., Comp. Biochem. Physiol. 10:1–16, 1963.
Smith, Homer W. J. Biol. Chem. 81:407–419, 1929.

Primary Examiner—Jill Warden
Assistant Examiner—Nancy J. Degen
Attorney, Agent, or Firm—Needle & Rosenberg

[57] ABSTRACT

A composition is provided, comprising purified alkaline gland fluid (AGF) from the alkaline gland of a cartilaginous fish. The invention also provides a purified protein of approximately 12 kD as determined by sodium dodecyl sulfate polyacrylamide gel electrophoresis under non-denaturing conditions, that decreases sperm motility and can be purified from the alkaline gland of a cartilaginous fish. Further provided are purified proteins that increase sperm motility and can be purified from the alkaline gland of a cartilaginous fish. Particularly, purified proteins of approximately 160 kD, approximately 32 kD and approximately 18 kD as determined by sodium dodecyl sulfate polyacrylamide gel electrophoresis (SDS-PAGE) under non-denaturing conditions increase sperm motility. A method of increasing sperm motility comprising the step of contacting sperm with an amount of the present purified AGF composition or purified proteins effective to increase the motility of the sperm is also provided. A contraceptive method is also provided that comprises the step of contacting sperm with an amount of the purified approximately 12 kD protein effective to inhibit the motility of the sperm.

10 Claims, 15 Drawing Sheets

ALKALINE GLAND FLUID PROTEINS AND METHODS OF ENHANCING AND INHIBITING SPERM MOTILITY

This invention was made with government support under NSF grant 8903369 awarded by the National Science Foundation. The government has certain rights in the invention.

BACKGROUND OF THE INVENTION

In the United States, at least 10% of couples suffer involuntarily infertility. In Britain, there are about 600,000 infertile couples (Winston, 1991) and in the United States two million women are potential candidates for in vitro fertilization (IVF). Because IVF has a low success rate of 10—15%, multiple attempts and increasing costs are incurred to bring a pregnancy to term. Therefore, only a tiny proportion of the North American and European population currently in need can take advantage assisted reproductive treatments. The situation for infertile people is much worse in less medically developed countries.

Poor function of spermatozoa accounts for one quarter of all human infertility: IVF is one of the only effective treatments (Winston and Handyside, 1993). IVF can be done by transfer of oocytes and sperm in a synthetic medium into the fallopian tube (gamete intrafallopian transfer (GIFT)) or newly fertilized zygotes (egg and sperm put into a synthetic medium and fertilization allowed to proceed) are transferred into the fallopian tube (zygote intrafallopian transfer (ZIFT).

Pregnancy resulted from only a small percentage (13%) of transfers of a single presumably fertilized egg back into the female, but rose to 25% when four or more eggs were simultaneously transferred (Winston and Handyside (1993)). One of the primary reasons for the low rates of pregnancy resulting from IVF is believed to be inadequate culture media in which the egg and sperm are kept.

In IVF, poor sperm function does not allow enough sperm to contact and penetrate the egg. Most previous strategies to overcome the difficulties of IVF have involved various manipulations of the oocyte. For example sperm have been injected directly into the egg with a high success rate (Fishel and Timson, 1992). The disadvantages include potential damage to the chromosome spindle and high genetic risks, because abnormal sperm may be injected. Furthermore this technique increases patient cost dramatically, because of the time and expertise necessary to perform this operation, which frequently must be repeated multiple times.

Only recently has attention turned to enhancement of sperm motility parameters. It has been shown that sperm motility parameters are important for both presenting the maximum number of male gametes to the egg as well as facilitating penetration through its zona pellucida (Bedford et al. 1982). Sperm motility parameters have a high correlation with fertilization rates in vitro (Mahadevan and Trounson, 1984).

The only compound currently used to enhance sperm motility in vitro or in vivo is pentoxifylline whose efficacy is currently questioned. Pentoxifylline (3-7 dimethyl-1-5-oxohexylxanthine) is added routinely to spermatozoa in human IVF programs. Its efficacy is hotly debated in the scientific literature, since one study reported that it was not useful in enhancing sperm function in cases with previous IVF failure (Tournaye et al. 1993). Furthermore, two recent studies have indicated that pentoxifylline causes spermatic mutagenesis as does direct application of caffeine to these gametes (Barkay et al. 1984 and Harrison et al. 1980).

Another study showed that oral administration increased sperm count and motility, but suggested that the effect may not have been any greater than that produced by ingestion of drinks containing caffeine, also a methylxanthine.

Although pentoxifylline did not increase sperm motility parameters in normospermic men, it had significant increases in these parameters in oligospermic samples. Nevertheless, when this drug was added to sperm from donors with a history of previously failed fertilization, there was only a 5.1% increase in the oocyte fertilization rate from 17.6 in controls to 22.7% in pentoxifylline-treated groups (Yovich et al. 1988). Also, recent studies have shown that pentoxifylline can only enhance significantly the fertilization rate when used within a brief time (30 minutes) prior to exposure to the egg. An added difficulty is that after incubation with pentoxifylline the sperm must be washed free of pentoxifylline and re-added to the oocyte due to the potential harmful effect of this drug on the egg (see Yovich et al. 1988).

There are currently no drugs other than pentoxifylline which are approved by the FDA for sperm motility enhancement. Furthermore, there are only scattered reports in the literature that other compounds are being tested. These include plasminogen activator, an endogenous protease, correlated positively with sperm motility (Lison et al. 1993), but there is no data suggesting a cause and effect relationship between the two. Acrosin, another endogenous protease in sperm, has no significant effect on sperm motility (Koukoulis et al. 1989) even though lower levels of this enzyme appear to be correlated with some abnormal semen characteristics (De Jong et al. 1993). Components of the oocyte may affect the fertilization rate (Hoshi et al. 1993; Winston and Handyside 1993) once the sperm and egg are in close proximity, but there currently are no data showing that these components enhance sperm motility. Hyaluronate and strontium added to the media slightly prevented sperm motility degradation (Psalti et al. 1993).

Male skates and rays have an accessory sex gland that produces a fluid (AGF) of alkaline pH (8-9) (Smith 1929). Prior to the present disclosure, the functions of this gland and the alkaline gland fluid were unknown.

The increased use of in vitro fertilization techniques by couples unable to bear children show a strong need for the use of the compositions and methods of the present invention, which will enhance sperm motility parameters and, thus, lead to greater oocyte fertilization. Artificial insemination programs for livestock also need the benefit of enhanced sperm motility. Likewise, there is also a need for a natural contraceptive for use in human vaginal contraceptive jellies and on condoms, because the current synthetic chemicals have either limited effectiveness or unknown long-term health effects. The present invention meets these needs by providing purified alkaline gland fluid and specific proteins that stimulate or decrease sperm motility.

SUMMARY OF THE INVENTION

A composition is provided, comprising purified alkaline gland fluid (AGF) from the alkaline gland of a cartilaginous fish. The invention also provides a purified protein of approximately 14 kD as determined by sodium dodecyl sulfate polyacrylamide gel electrophoresis under non-denaturing conditions, that decreases sperm motility. Further provided are purified proteins that increase sperm motility. Particularly, purified proteins of approximately 350 kD, approximately 40 kD and approximately 22 kD as determined by sodium dodecyl sulfate polyacrylamide gel electrophoresis (SDS-PAGE) under non-denaturing conditions increase sperm motility. A method of increasing sperm motility comprising the step of contacting sperm with an amount of the present purified AGF composition or purified proteins effective to increase the motility of the sperm is also provided. A contraceptive method is also provided that comprises the step of contacting sperm with an amount of the purified approximately 14 kD protein effective to inhibit the motility of the sperm.

DETAILED DESCRIPTION OF THE INVENTION

Figure 1A:
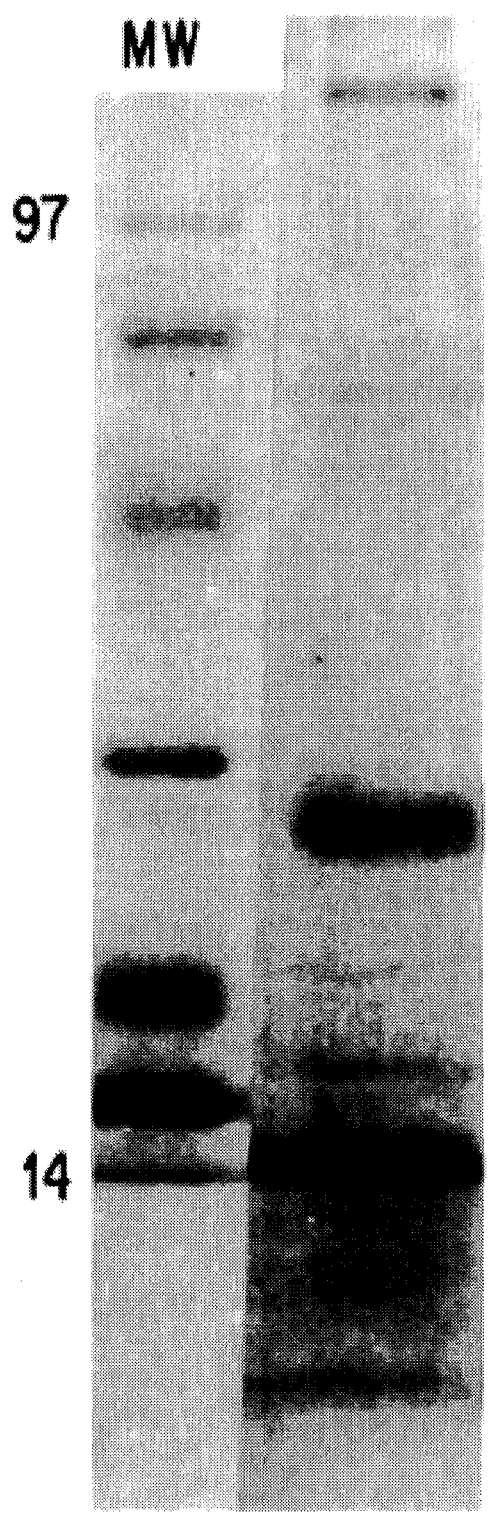
FIG. 1A a polyacrylamide gel of alkaline gland fluid (AGF) under non-denaturing conditions.

This invention provides a composition comprising purified alkaline gland fluid (AGF) from the alkaline gland of a cartilaginous fish. As used to describe the AGF, the term "purified" refers to AGF from which some necrotic and viable sperm as well as membrane fragments and cellular debris have been removed. The removal of these components of whole AGF can be accomplished by centrifugation, among other methods.

Cartilaginous fish (class chondrichthyes) include rays, skates, sharks and chimaeras. The present invention teaches that the AGF from the alkaline glands of skates and rays, and certain proteins in the AGF, have sperm motility increasing or decreasing effects. Other animals with alkaline glands or animals with homologous organs that produce fluids with homologous proteins, can be expected to provide compositions and proteins for use in the present invention.

The invention also provides a purified protein of approximately 14 kD as determined by sodium dodecyl sulfate polyacrylamide gel electrophoresis under nondenaturing conditions, that decreases sperm motility. As used to describe the individual proteins of the invention, "purified" means the protein is sufficiently free of contaminants, cell components or other AGF proteins with which the protein normally occurs to distinguish the protein from the contaminants or components. As provided in the Examples SDS-PAGE followed by elution can be used to obtain the purified proteins of the present invention. Methods of purifying the present proteins to homogeneity include high performance liquid chromatography, as well as two dimensional gel electrophoresis.

The term "motility" unless otherwise specified, describes % motility, which is the percentage of the total number of sperm assessed that fall within all World Health Organization (WHO) categories of motility except the category designated "no motility" regardless of velocity or directionality. It should be understood that other standardized measures of sperm motility parameters can also be used. Other measures of sperm motility include "velocity" and "linearity" which can be assessed using automatic semen analyzers as described in the Examples. A decrease in sperm motility, as contemplated herein, constitutes a statistically significant reduction in the motility of sperm.

A composition comprising the approximately 14 kD protein and a pharmaceutically acceptable carrier is also contemplated. By "pharmaceutically acceptable" is meant a material that is not biologically or otherwise undesirable, i.e., the material may be administered to gametes in vivo or in vitro along with the selected protein without causing any undesirable biological effects or interacting in a deleterious manner with any of the other components of the pharmaceutical composition in which it is contained.

The above protein composition can also include a spermicide. The spermicide can be selected from among the numerous well known spermicidal compounds, such as NONOXYL-9.

Further provided is are purified proteins that increase sperm motility. Particularly, purified proteins of approximately 350 kD, approximately 40 kD and approximately 22 kD as determined by sodium dodecyl sulfate polyacrylamide gel electrophoresis (SDS-PAGE) under non-denaturing conditions increase sperm motility. The purification of these proteins from AGF is exemplified in the Examples.

The invention also provides nucleic acids encoding the proteins of the invention. Given the present teaching regarding the purification of the subject proteins, one skilled in the art, using routine methods, can obtain the nucleic acids encoding the proteins. For example, a DNA library generated from alkaline gland DNA can be screened for clones expressing the present AGF proteins. Once such clones are located, their DNA can be sequenced and the coding sequence for the expressed protein determined. Alternatively, a partial sequence of the protein (e.g., by N-terminal sequencing) can be used to generate a set of nucleic acid probes that can be used to detect larger DNA molecules that encode the protein. These molecules can then be sequenced using well known methods. For nucleic acid manipulations, see Sambrook et al. (*Molecular Cloning: A Laboratory Manual*, 2nd Ed., Cold Spring Harbor Laboratory, Cold Spring Harbor, N.Y. 1989).

Also provided are active fragments of the purified proteins of the invention. A fragment of the protein can be isolated from the whole protein by chemical or mechanical disruption. The purified fragments thus obtained can be tested to determine their activity by the methods taught herein. Fragments of the protein can also be synthesized directly once the amino acid sequence is determined. The fragments of the present invention can also be recombinant proteins obtained by cloning nucleic acids encoding the protein in an expression system capable of producing the protein or fragments thereof. As described above, the proteins and fragments of the invention can be used in conjunction with a pharmaceutically acceptable carrier for delivery to the subject.

A method of increasing sperm motility comprising the step of contacting sperm with an amount of the present purified AGF composition effective to increase the motility of the sperm is also provided. An increase in sperm motility, as contemplated herein, constitutes a statistically significant increase in the motility of sperm as defined above. The contacting step can take place in vitro, as in any of the well known IVF methods, for example. In the methods of increasing sperm motility, the contacting step can also take place in vivo. For example, intravaginal administration by means of a suppository or other solid, liquid, gel or lotion carrier.

A method of increasing sperm motility comprising the step of contacting sperm with an amount of any of the purified proteins of approximately 160 kD, approximately 40 kD and approximately 22 kD effective to increase the motility of the sperm. Alternatively, purified mixtures of the sperm motility increasing proteins of the invention can be used in the method. In this method of increasing sperm motility, like the method using purified AGF, the contacting step can take place in vitro or in vivo.

A contraceptive method is also provided that comprises the step of contacting sperm with an amount of the purified approximately 14 kD protein effective to inhibit the motility of the sperm. The inhibition of sperm motility reduces the likelihood of fertilization of an ovum. The contacting step of this method can take place intravaginally. For example, the protein can be a component of or used in conjunction with vaginal jellies, foams, sponges, suppositories and condoms, as such combinations, using conventional contraceptives, are well understood in the art. Alternatively, a timed release, scrotally implanted vehicle can be provided for in vivo delivery of the contraceptive protein directly to the vas deferens or seminal vesical of the male.

The following examples are intended to illustrate, but not limit, the invention. While the protocols described are typical of those that might be used, other procedures known to those skilled in the art may be alternatively employed.

EXAMPLES

Stingray Sperm and Alkaline Gland Fluid Collection.

Male Atlantic stingrays (DaSyatis sabina) captured in the Charleston Harbor estuary were housed in a 16,000 liter holding tank. The stingrays were allowed to acclimate for at least five days before experimentation, and were fed a regular diet of shrimp. Water in the holding tank was drawn from the Charleston Harbor (approximately 650 mOsm/L) and maintained at 70° C.

Stingrays were anesthetized with 3-aminobenzoic acid ethyl ester (0.5 g/liter of sea water, Sigma Chemical Co., St. Louis, Mo.). The abdominal cavity was opened, the viscera retracted, and the peritoneum stripped from the vas deferens and alkaline glands. A 5 ml sterile syringe with a 21 gauge needle was used to aspirate alkaline gland fluid (AGF), which was initially stored at −20° C. and later at −80° C. for long term storage. To obtain the purified AGF of the present invention, the frozen whole AGF was thawed and samples were centrifuged for 5 min at 2500 rpm to remove some large fragments, including viable and necrotic sperm.

Sperm was aspirated from the vas deferens using a 16 gauge needle, and a 5 ml sterile syringe. At no time was sperm exposed to extraneous body fluids other than that present in the vas deferens. Aspirated sperm was immediately diluted with elasmobranch Ringer solution (NaCl, 280.0 mM; KCl, 5.0 mM; $MgCl_2$, 3.3 mM; $CaCl_2$, 3.8 mM; $NaHCO_3$, 10.0 mM; urea, 350.0 mM; dextrose, 5.0 mM; 800 mOsm/L; pH 8.2) containing 5.0 mg bovine serum albumin (BSA)/ml. The sample was then washed twice by centrifugation at 200 g for ten minutes. After washing, sperm was diluted to approximately 25 million sperm/ml in elasmobranch Ringer solution with 5 mg BSA/ml. The concentration of stingray sperm was determined from the number of sperm from a 10 μl sample in five quadrants of a Neubauer hemacytometer, with a depth of 0.1 mm (Baxter Healthcare Corp., McCaw Park, Ill.).

Human Sperm.

Human volunteers donated sperm by masturbation into a sterile receptacle, which was allowed to liquefy for one hour before analysis. Volunteers were instructed to abstain from sexual activity for at least two days prior to sperm donation. The collected sample was then diluted with sperm washing media with 5.0 mg human albumin/ml (Catalog No. 9983, Irvine Scientific, Santa Ana, Calif.), centrifuged at 200 g for ten minutes, the supernant drawn off, the pellet resuspended and washed once more, and finally diluted in washing media at a concentration of 50 million sperm/ml.

Alkaline Gland Fluid Protein Separation (Denatured).

Aspirated AGF samples were thawed at 4° C., and total protein concentrations were determined using Lowry's method (Sigma diagnostic kit #690, St. Louis Mo.). The total amount of protein in AGF aspirated from stingrays was 112.1 ±11.2 mg/ml (n=7). Five different samples were pooled, and concentrated two fold in a Minicon-B15 protein concentrator (Amicon Corp., Lexington, Mass.) at 4° C. Concentrated samples and molecular weight markers were then denatured for SDS-PAGE, by boiling 10 minutes with 2.0% SDS and 2.0% 2-mercaptoethanol ( 1:1 dilution ).

Denatured AGF samples and molecular weight markers (25 μl) were loaded into wells of the stacking gel (4.5% acrylamide, 1.5 mm thick). A 7.5%–15% acrylamide gradient gel was used for the separating gel, at a thickness of 1.5 mm using a SE400 Vertical Slab Gel Unit (Hoefer Scientific Instruments, San Francisco). The running buffer was Tris HCl containing 0.4% SDS (pH 8.8). The SDS-PAGE was run for four hours at 45 mA/110 V using a PS 500 xDC power supply (Hoefer Scientific Instruments, San Francisco, Calif.). The resultant gel was removed from its glass plates, stained for 15 minutes with 0.1% Coomassie Blue, and destained overnight. Molecular weights of separated proteins were then determined using the respective $R_f$ values of AGF protein bands, compared against those of molecular markers. All electrophoresis supplies were purchased from Baxter Healthcare Corp. (McGaw Park, Ill.).

Separation of AGF proteins by SDS-PAGE under denaturing conditions yielded 9 separated bands. The 9 bands separated out in 3 distinct groups. Bands 1–3 formed a high molecular weight group of 250, 155, and kD, respectively. Bands 4 and 5 formed a group having molecular weights of 70 and 62 kD, and bands 6 and 7 formed a group having molecular weights of 38.5 and 37 kD, respectively. Band 8 had a molecular weight of 25 kD, and band 9 a molecular weight of 16 kD.

Alkaline Gland Fluid Protein Purification (Non-denatured)

Twelve AGF samples were pooled and concentrated five fold using the Minicon-B15 as described above. One hundred microliters of non-denatured AGF sample was loaded into two gels similar to that described above for SDS-PAGE. One gel was loaded with non-denatured samples and molecular markers, and the other with non-denatured samples. The running buffer was Tris HCl without SDS, and both gels were run at room temperature for four hours at 45 mA/110 V. The gel with the molecular markers was stained with Coomassie Blue, for 15 minutes and destained for one hour.

Figure 1B:
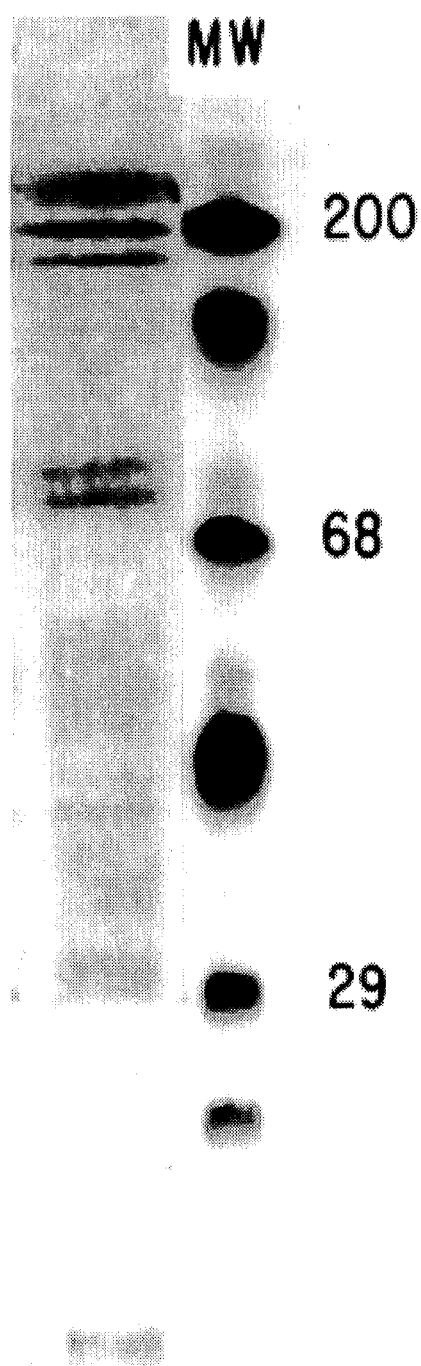
FIG. 1B shows a polyacrylamine gel of AGF under denaturing conditions.

Purification of AGF proteins by SDS-PAGE under non-denaturing conditions yielded 5 separated bands with the following molecular weights: band 1, MW 350 kD; band 2, MW 40 kD; band 3, MW 22 kD; band 4, MW 14 kD; and band 5, MW 40 kD (FIG. 1). Bands 3–5 were apparently responsible for the brown pigmentation of AGF, because they were dark brown, and easily distinguished without prior staining. After staining with Coomassie Blue, these bands took on the same coloration as bands 1 and 2.

The gel with only the non-denatured samples was then removed from its glass plates, and individual bands were sliced out using the stained gel as a guide. Each isolated band was placed in its own separate tube, and placed in an ElectroEluter: Model 422 (BIO-Rad Lab., Richmond, Calif.). The elution process lasted five hours, with Tris HCl running buffer with a 0.4% SDS, at 10 mA/24 V using BIO-RAD power supply (model 500/200). Each isolated protein was dialyzed for 24 hours in three changes of Tris HCl (pH 8.8) at 4° C., using dialysis tubing with a 6000–8000 MW cutoff (Spectrum Medical Industries, Inc., Los Angeles, Calif.). The protein concentrations were determined using Lowry's method (Sigma diagnostic kit #690, St Louis, Mo.) for each purified sample. The samples were then stored at −20° C. until used for sperm analysis.

Stingray Sperm Analysis.

(1) Treatment with AGF.

Washed stingray sperm samples were exposed to five different treatments for a period of ten hours. The treatments included: 1) elasmobranch Ringer solution +5 mg BSA/ml, 2) elasmobranch Ringer solution +100 mg BSA/ml, 3) AGF, 4) denatured AGF, and 5) synthetic AGF (described below) +sucrose. All treatments were adjusted to an osmolarity equivalent to that of AGF (approximately 810 mOsm), and a pH of 8.2–8.3. Synthetic AGF includes the ionic constituents of AGF (NaCl, 102.5 mM; KCl, 2.0 mM; $MgCl_2$, 2.4 mM; $NaHCO_3$, 204.0 mM; urea, 116.1 mM) with the osmolality adjusted using a saturated sucrose solution. Each treatment was diluted with one part elasmobranch Ringer solution containing 5.0 mg BSA/ml, and one part washed sperm suspension. A 10 μl sample of each treatment was placed in a Neubauer hemacytometer, with a depth of 0.1 mm (Baxter Healthcare Corp., McGaw Park, Ill.). One hundred spermatozoa were assessed using the World Health Organization (WHO) rating system (Glover et al. 1990), every two hours during a ten hour period. Spermatozoa were rated as: 0=no motion (dormant or "non-motile"), 1=in loco motion (lack of forward motion or "non-progressive motility"), 2=slow progression (traversing <10 μm/s), 3=moderate progression (traversing between 10–30 μm/s), 4=fast progression (traversing >30 μl m/s.

Figure 2:
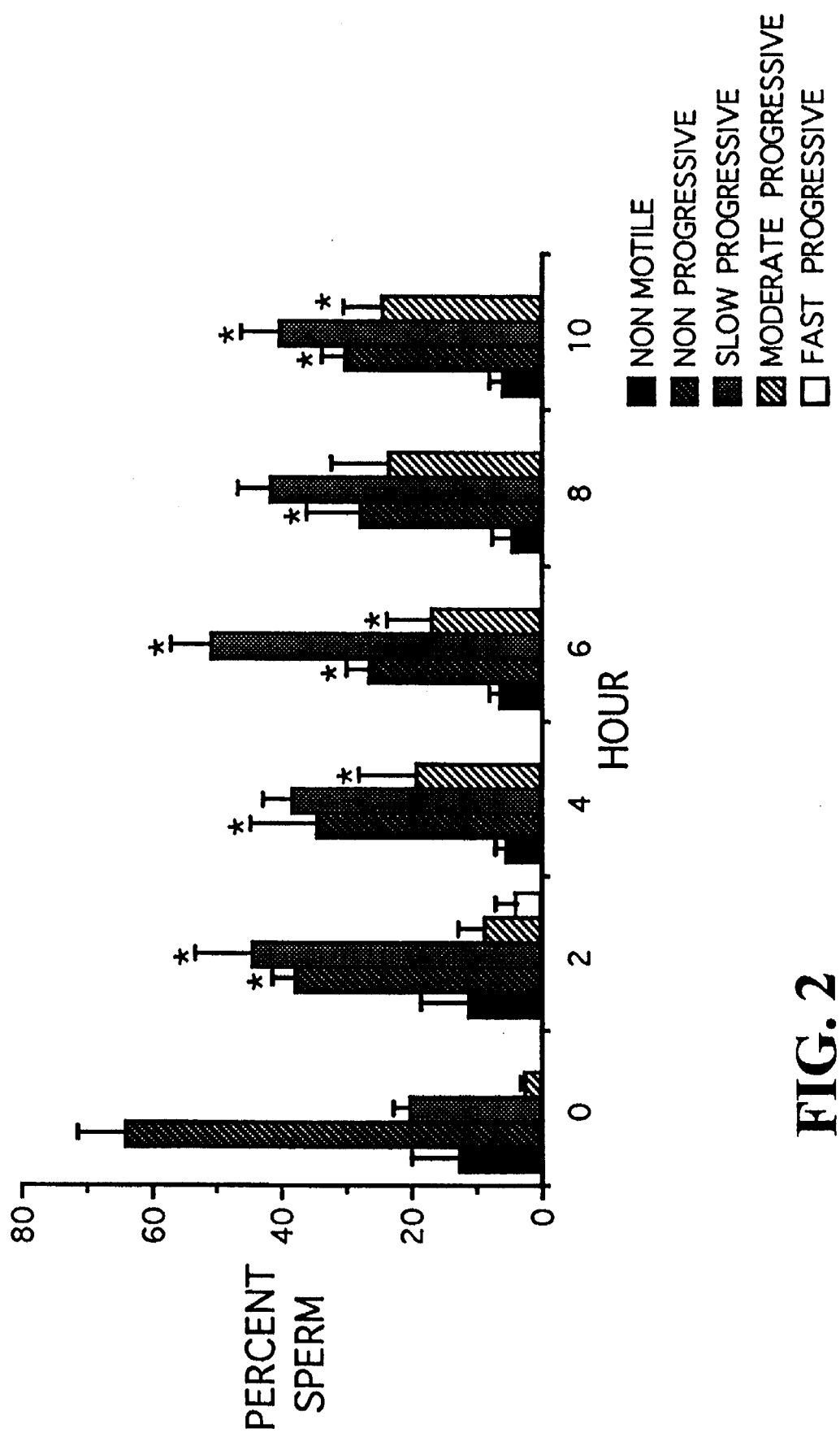
FIG. 2 is a bar graph showing the effects of AGF on stringray sperm. The asterisk (*) indicates significant change in sperm motility from initial rates obtained at hour 0 (n=4 stingrays, Means ±SE, p>0.05).

The effects of non-denatured AGF on stingray sperm are shown in FIG. 2. In those sperm exposed to AGF, the number of non-motile sperm did not change significantly from time 0 throughout the ten hour experiment. Sperm with non-progressive motility decreased 45.8% within 4 hours and reached its lowest level at hour 6 with a 58.8% decrease. At hour 10, the number of sperm with non-progressive motility was 56.0% of the original value at time 0. Those sperm with slow progressive motion increased 121.3% within 2 hours and reached their highest level at hour 6 with an increase of 152.5%. The greatest degree of change was seen in sperm with moderate progressive motion (FIG. 2). At hour 10, these sperm increased more than ten fold over their original numbers at time 0. Overall, it appears that AGF stimulates progressive motion in stingray sperm with a corresponding decline in the number of sperm with non-progressive motion.

Figure 3:
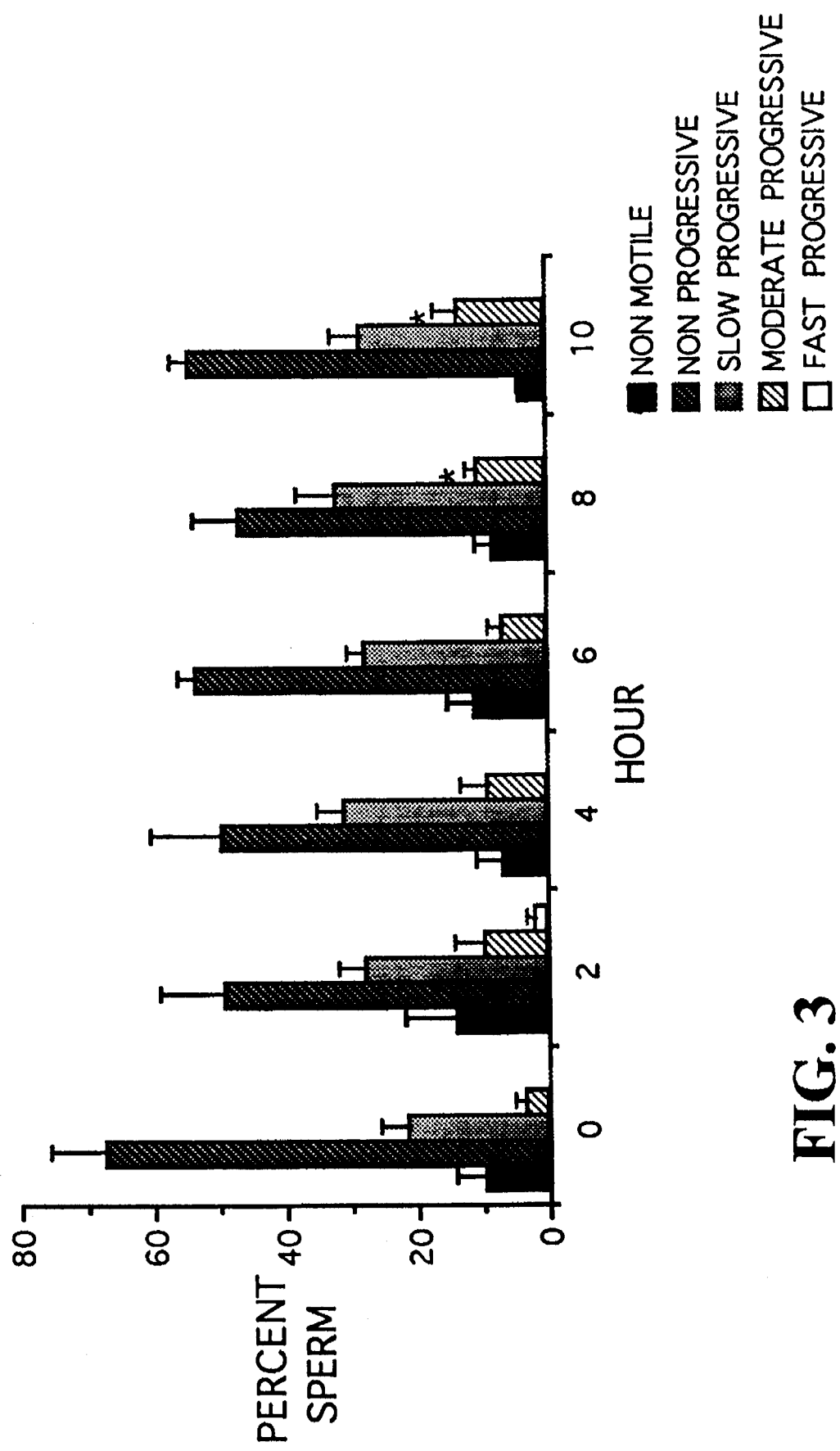
FIG. 3 is a bar graph showing the effects of denatured AGF on stingray sperm. The asterisk (*) indicates significant change in sperm motility from initial rates obtained at hour 0 (n=4 stingrays, Means ±SE, p>0.05).

Stingray sperm exposed to denatured AGF did not demonstrate a significant change in the number of sperm with no motion, non-progressive motion, and slow progressive motion (FIG. 3). The only significant difference in the denatured AGF treatment was noted in sperm with moderate progression at hours 8 and 10 (FIG. 3). The number of moderately progressive sperm during these hours increased 107.7% and 307.7%, respectively, from initial numbers at time 0. There was no significant difference between rating categories of denatured AGF (FIG. 3) with those of either elasmobranch Ringer solution with 5 and 100 mg BSA/ml (FIGS. 4 and 5, respectively), as well as between the categories of the latter two treatments.

Figure 4:
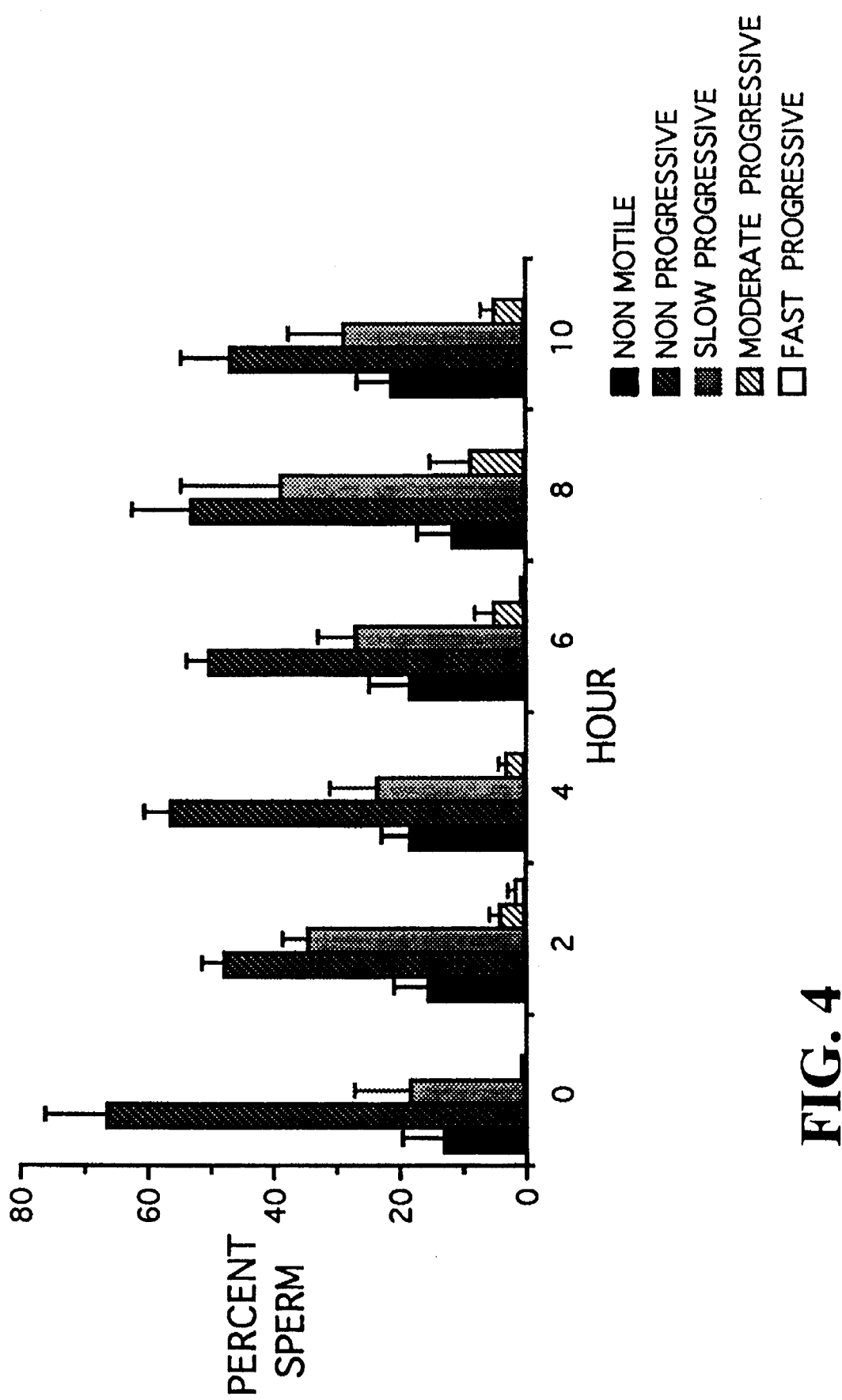
FIG. 4 is a bar graph showing the effects of elasmobranch Ringer solution +5 mg BSA/ml on stingray sperm. There was no significant change in sperm motility from initial ratings at time 0 (n=4 stingrays, Means±SE, p>0.05).
Figure 5:
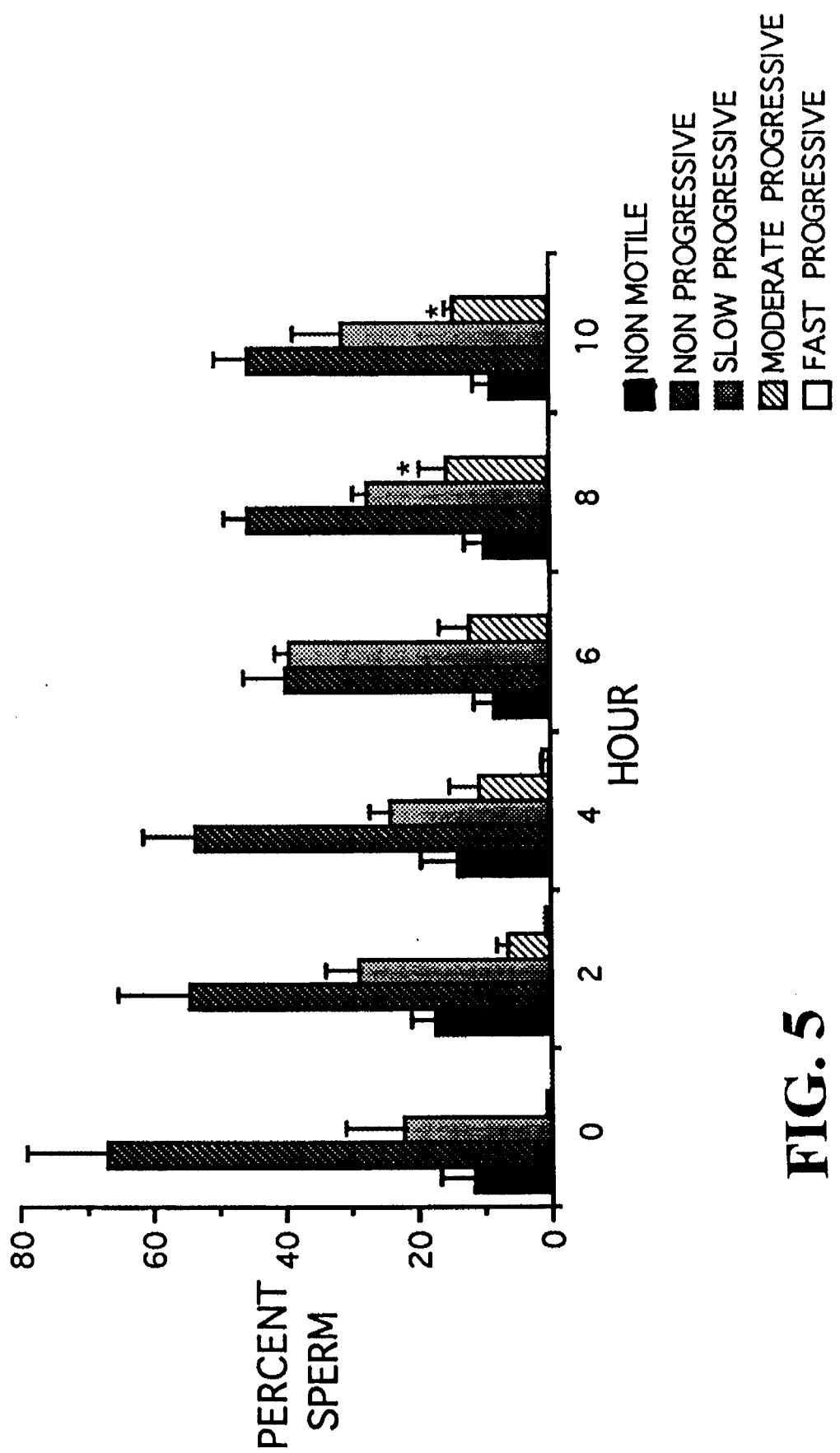
FIG. 5 is a bar graph showing the effects of elasmobranch Ringer solution +100 mg BSA/ml on stingray sperm. The asterisk (*) indicates significant change in sperm motility from initial rates obtained at hour 0 (n=4 stingrays, Means ±SE, p>0.05).

Comparison of the five rating categories of AGF treatments (FIG. 2) with those of denatured AGF (FIG. 3) and elasmobranch Ringer solution with 5 and 100 mg BSA/ml (FIGS. 4 and 5, respectively) resulted in a significant difference among all rating categories except those sperm with fast progressive motion. Significant differences between categories were resolved with comparisons between hourly time points within rating categories of the various treatments. The number of slow progressive sperm within AGF treatments (FIG. 2) were 40% and 30% higher after ten hours than those in denatured AGF (FIG. 3) and elasmobranch Ringer solution with 100 mg BSA/ml (FIG. 5), respectively. At hour six, the number of slow progressive sperm was up to 80% higher in AGF treatments (FIG. 2) than in elasmobranch Ringer solution with 5 mg BSA/ml (FIG. 4). After 6 hours, sperm with non-progressive motion were 50–79% lower in AGF treatments than in any other treatment.

Figure 6:
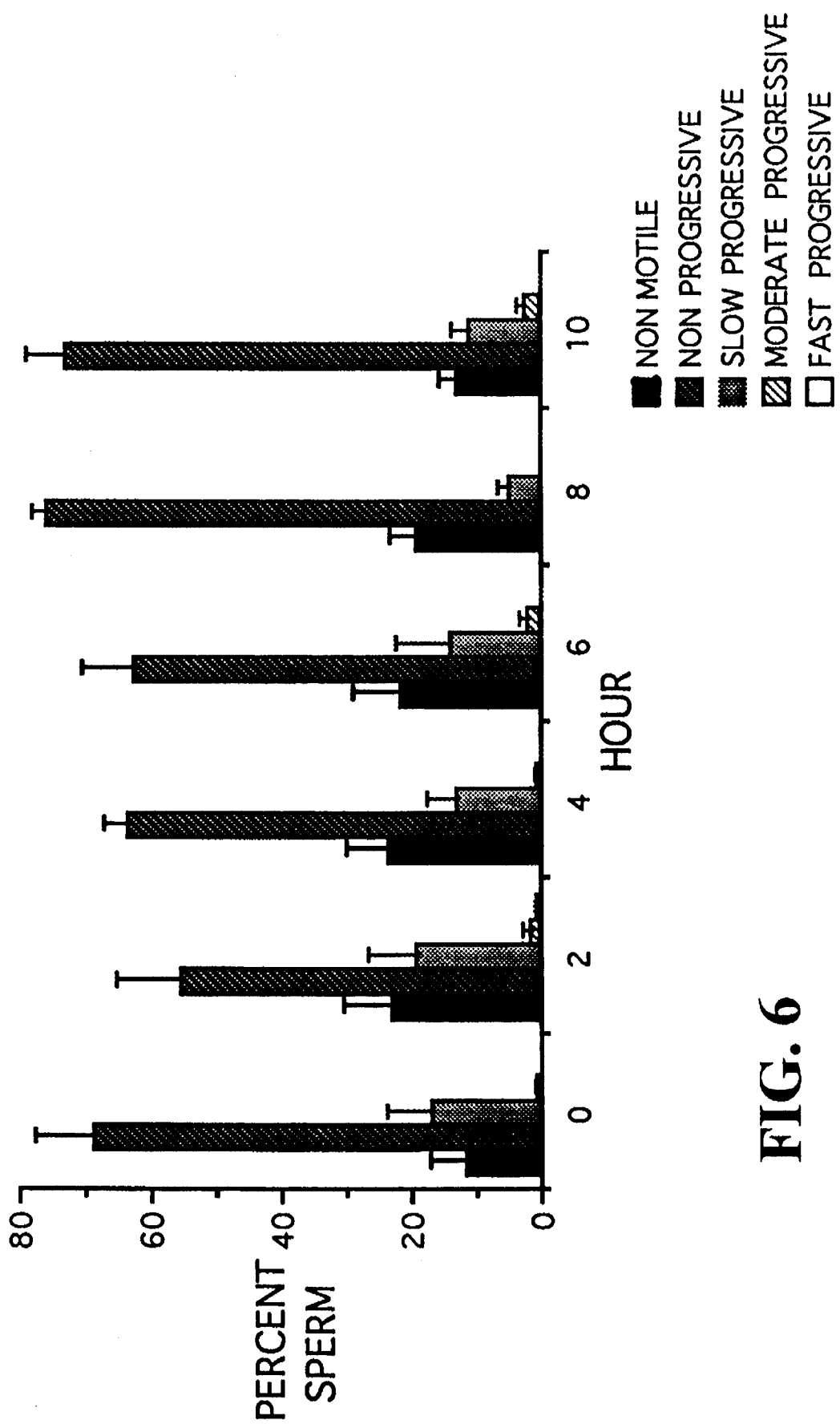
FIG. 6 is a bar graph showing the effects of synthetic AGF modified with sucrose on stingray sperm. There was no significant change in sperm motility from initial ratings at time 0(n=4 stingrays, Means ±SE, p>0.05).

Protein-free elasmobranch Ringer solution with its osmolarity adjusted to 800 mOsm/L with sucrose had no effect on stingray sperm (FIG. 6). Comparison of the mean number of sperm within each rating category over the ten hour time period of treatment with protein-free elasmobranch Ringer solution showed no significant change from initial levels at time 0. In contrast, sperm with non-progressive motion were 41.1% lower in AGF treatments, and sperm that were slow or moderately progressive were 272% and 977% higher in AGF treatments, respectively, than in protein-free elasmobranch Ringer solution (FIGS. 2 and 6). Compared to other treatments containing BSA, the number of sperm either without motion or with non-progressive motion are higher in protein-free Ringer solution, but those with slow progression are approximately 60% lower.

(2) Treatment with purified AGF proteins.

The WHO rating system was also applied to washed sperm samples exposed to purified AGF non-denatured proteins. Purified proteins were diluted to the original total protein concentration of AGF with elasmobranch Ringer solution containing 5.0 mg BSA/ml. Each purified protein sample was diluted with one part elasmobranch Ringer solution containing 5.0 mg BSA/ml and one part washed sperm suspension. These were assessed against a control consisting of two parts elasmobranch Ringer solution with 5.0 mg BSA/ml and one part washed sperm suspension. One hundred spermatozoa were randomly assessed every two hours during a period of ten hours.

Figure 7:
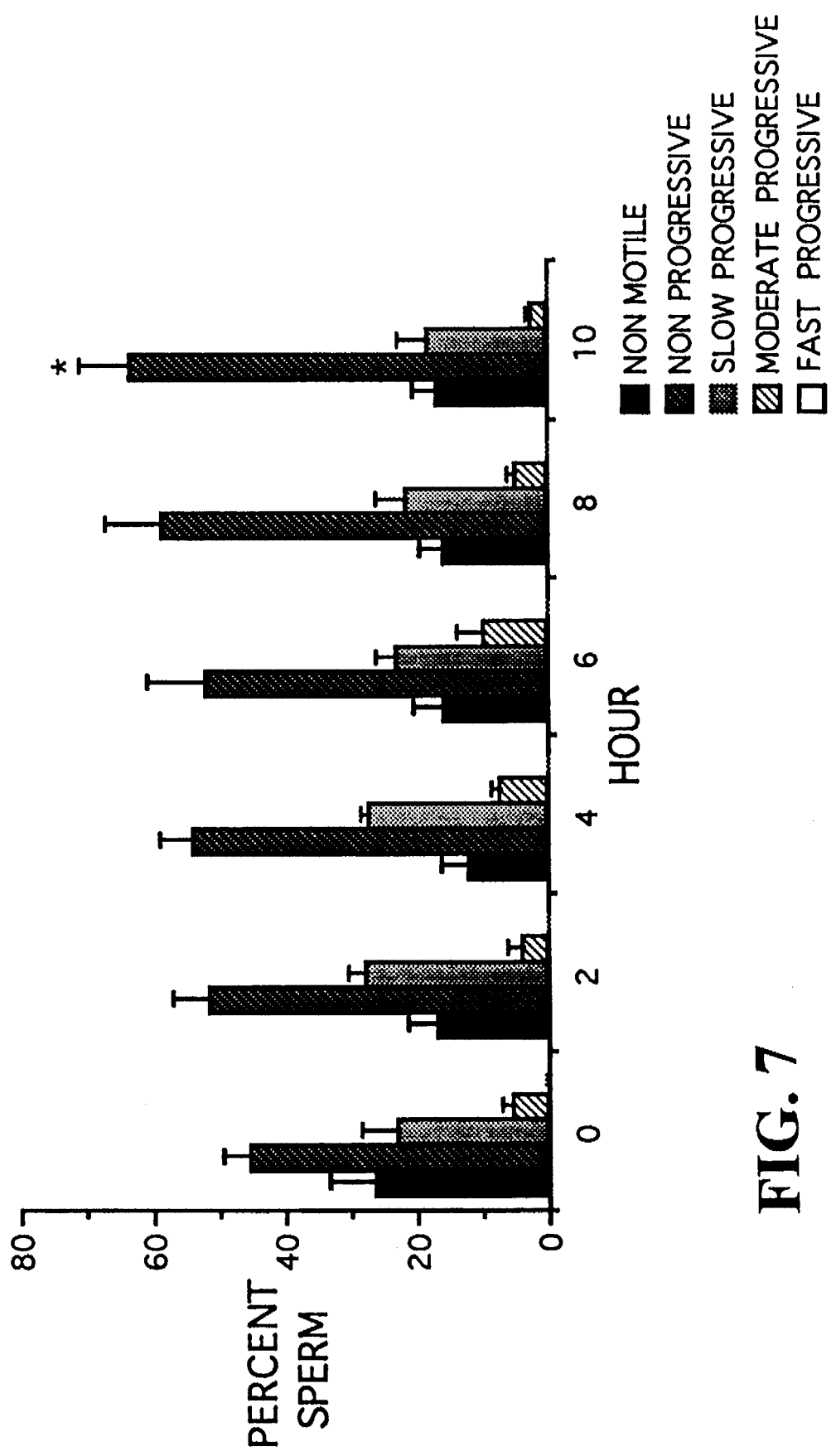
FIG. 7 is a bar graph of control conditions (elasmobranch Ringer solution +5 mg BSA/ml) used to determine significant changes in stingray sperm motility after exposure to isolated AGF proteins (FIGS. 8–12). The asterisk (*) indicates significant change in sperm motility from initial rates obtained at hour 0 (n=5 stingrays, Means ±SE, p>0.05).
Figure 8:
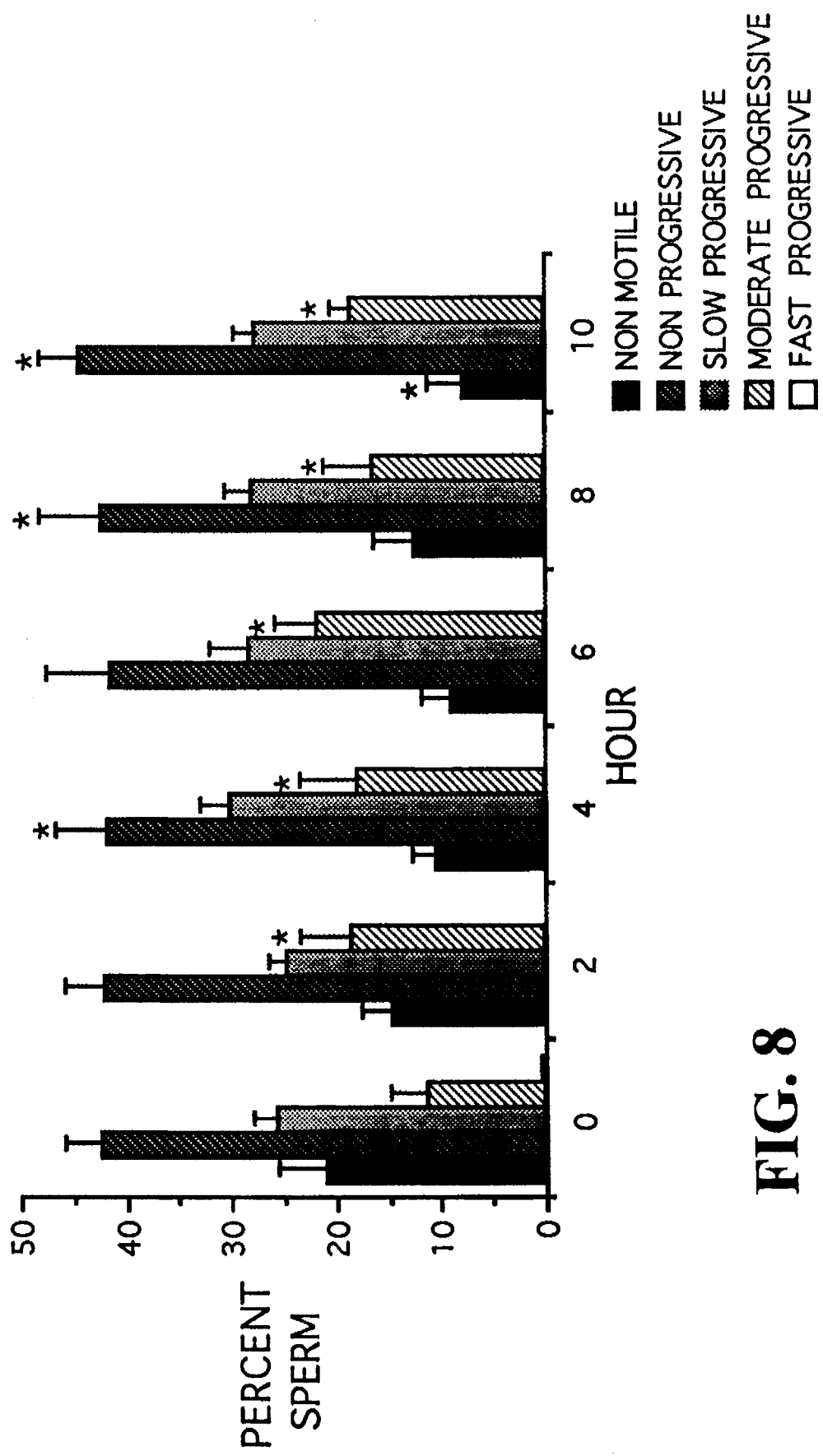
FIG. 8 is a bar graph demonstrating the motility distribution pattern of stingray sperm exposed to protein isolated from band 1 of AGF separated using non-denaturing PAGE. The asterisk (*) indicates a significant difference from control rates (FIG. 7) during the same time interval (n=5 stingrays, Means ±SE, p>0.05).
Figure 9:
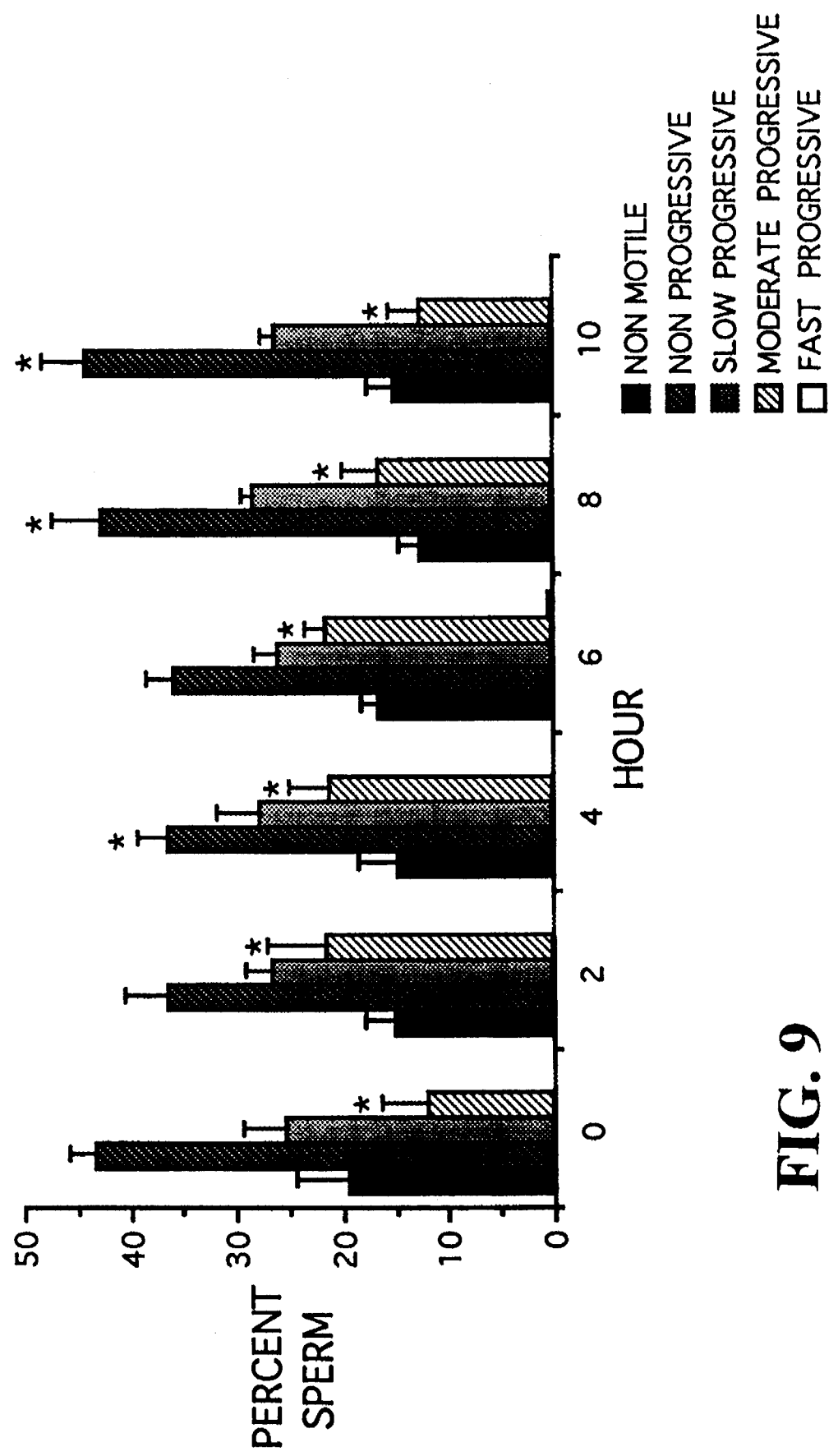
FIG. 9 is a bar graph demonstrating the motility distribution pattern of stingray sperm exposed to protein isolated from band 2 of AGF separated using non-denaturing PAGE. The asterisk (*) indicates a significant difference from control rates (FIG. 7) during the same time interval (n=5 stingrays, Means ±SE, p>0.05).
Figure 10:
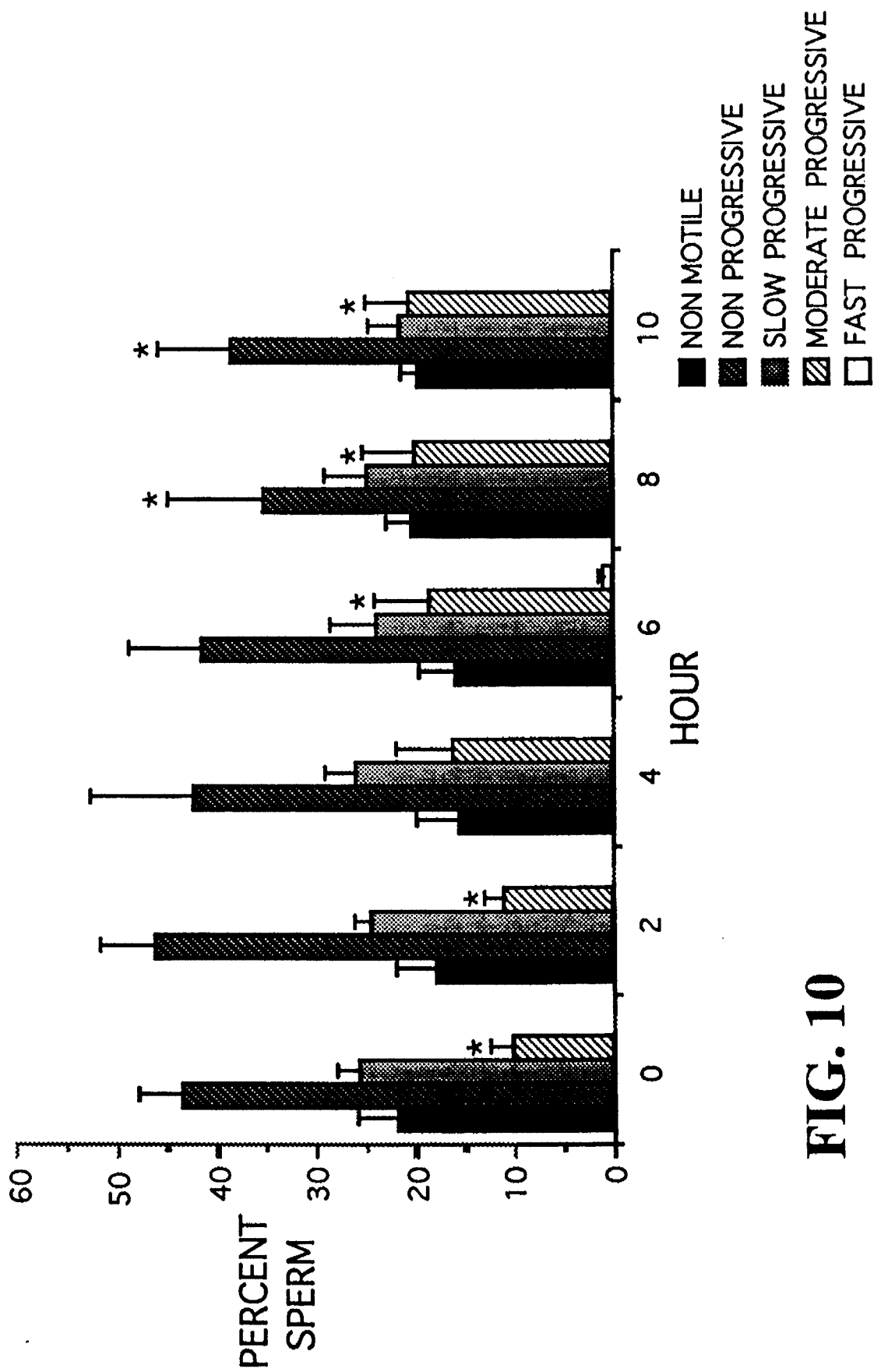
FIG. 10 is a bar graph demonstrating the motility distribution pattern of stingray sperm exposed to protein isolated from band 3 of AGF separated using non-denaturing PAGE. The asterisk (*) indicates a significant difference from control rates (FIG. 7) during the same time interval (n=5 stingrays, Means ±SE, p>0.05).

Exposure of stingray sperm to purified non-denatured AGF proteins was compared to control conditions (elasmobranch Ringer solution with 5 mg BSA/ml, FIG. 7). FIGS. 4 and 7 represent internal controls for two separate sets of experiments on stingray sperm, both of which demonstrate no significant change in sperm motility. Proteins 1–3 caused a significant decrease in the number of sperm with non-progressive motion ranging from 22% to 40% within 4–10 hours (FIGS. 8–10, respectively). The number of moderately progressive sperm was significantly higher throughout the entire ten hours when compared to control conditions. Increases in moderately progressive sperm compared to control conditions ranged 2.3–8.4 fold higher for protein 1 (FIG. 8), 2.3–5.4 fold higher for protein 2 (FIG. 9), and 9.1–21.9 fold higher for protein 3 (FIG. 10). Proteins 1–3 cause a shift from non-progressive sperm to those that are moderately progressive.

Figure 11:
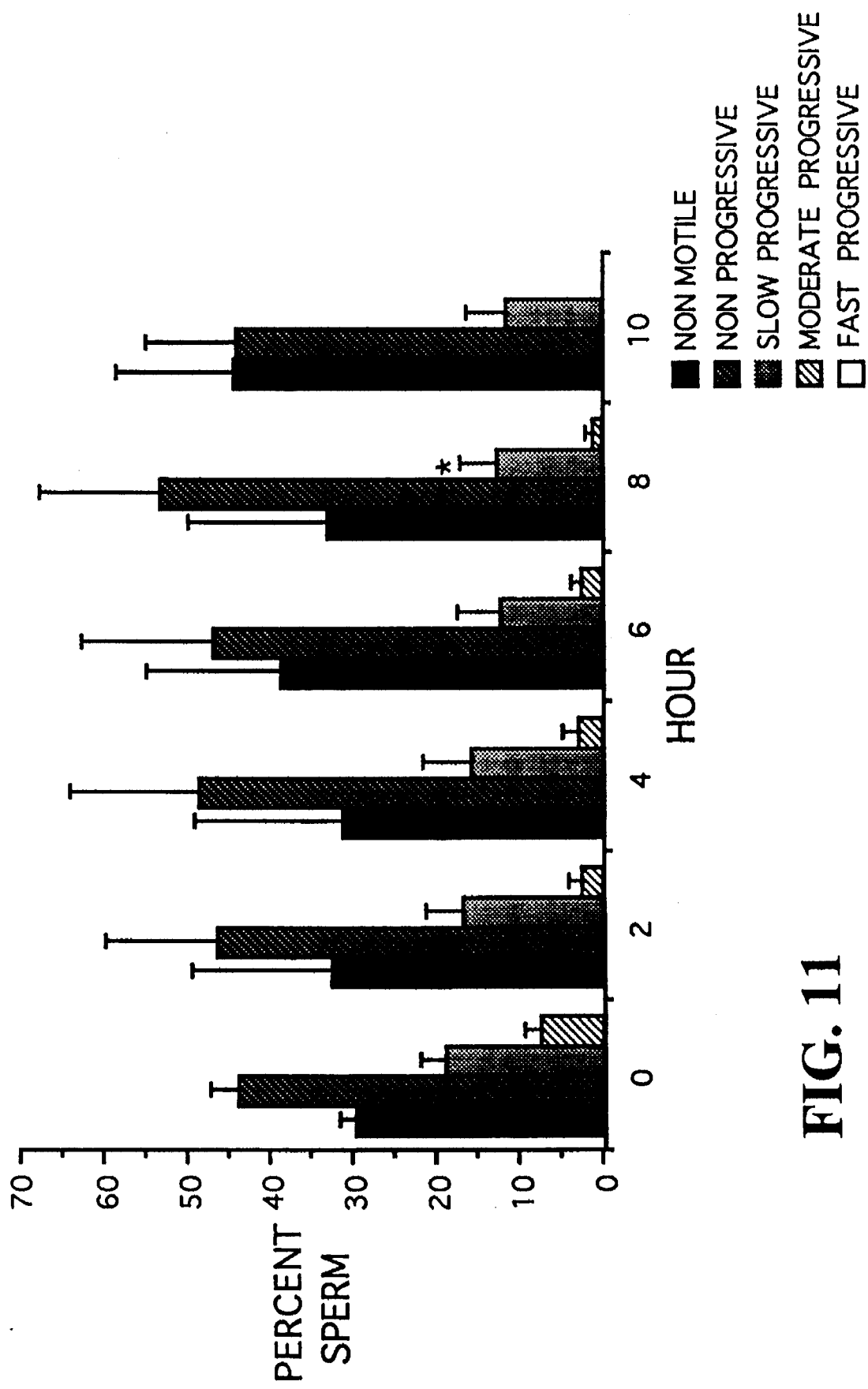
FIG. 11 is a bar graph demonstrating the motility distribution pattern of stingray sperm exposed to protein isolated from band 5 of AGF separated using non-denaturing PAGE. The asterisk (*) indicates a significant difference from control rates (FIG. 7) during the same time interval (n=5 stingrays, Means ±SE, P>0.05.)

Under control conditions, the number of sperm with non-progressive motion steadily increased to 28.4% higher than that at time 0 (FIG. 7). The other rating categories did not change significantly over time under control conditions, suggesting that the increase in non-progressive sperm was the result of an overall contribution from non-motile and motile sperm rather than a shift from a specific category. There was no significant difference between control conditions and the effects of protein 5 (FIGS. 7 and 11).

Figure 12:
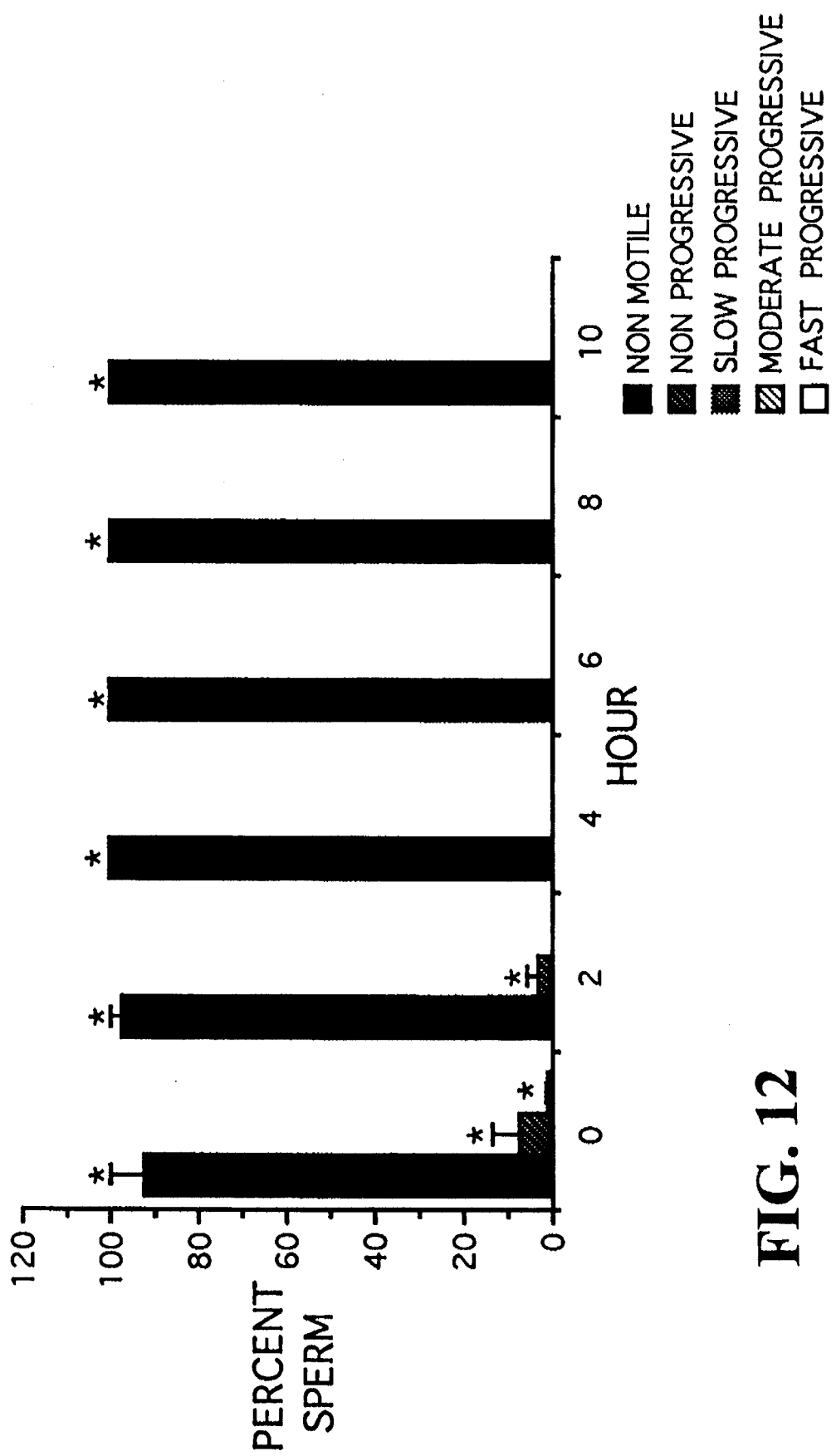
FIG. 12 is a bar graph demonstrating the motility distribution pattern of stingray sperm exposed to protein isolated from band 4 of AGF separated using non-denaturing PAGE. The asterisk (*) indicates a significant difference from control rates (FIG. 7) during the same time interval (n=5 stingrays, Means ±SE, p>0.05).

The most dramatic effect of AGF proteins was demonstrated with protein 4 (FIG. 12). Immediately upon addition of protein 4 to the sperm suspension, 92% of the sperm became non-motile. After 4 hours, all sperm became non-motile. These effects were obviously significantly different from those observed under control conditions and exposure to proteins 1–3. The presence of the BSA elasmobranch Ringers control groups establishes that this effect is AGF protein (peptide) specific and not due to the effects of constituents of the fluid or the mere presence of proteins.

Human Sperm Analysis.

Washed human sperm was initially exposed to diluted AGF, to determine the concentration required for further experimentation. AGF was diluted with sperm washing medium in the following ratios: 1:1, 1:2, 1:4, 1:8, and 1:16. One hundred microliters of each dilution was added to an equal amount of washed sperm. A 5 µl aliquot was removed every two hours for a total of ten hours and assessed for velocity, linearity, and percent motility using a Cell Soft Semen analyzer (CyroResources, Montgomery, N.Y.). A total of 100 spermatozoa were assessed for each dilution every two hours during the ten hour experiment.

Figure 13:
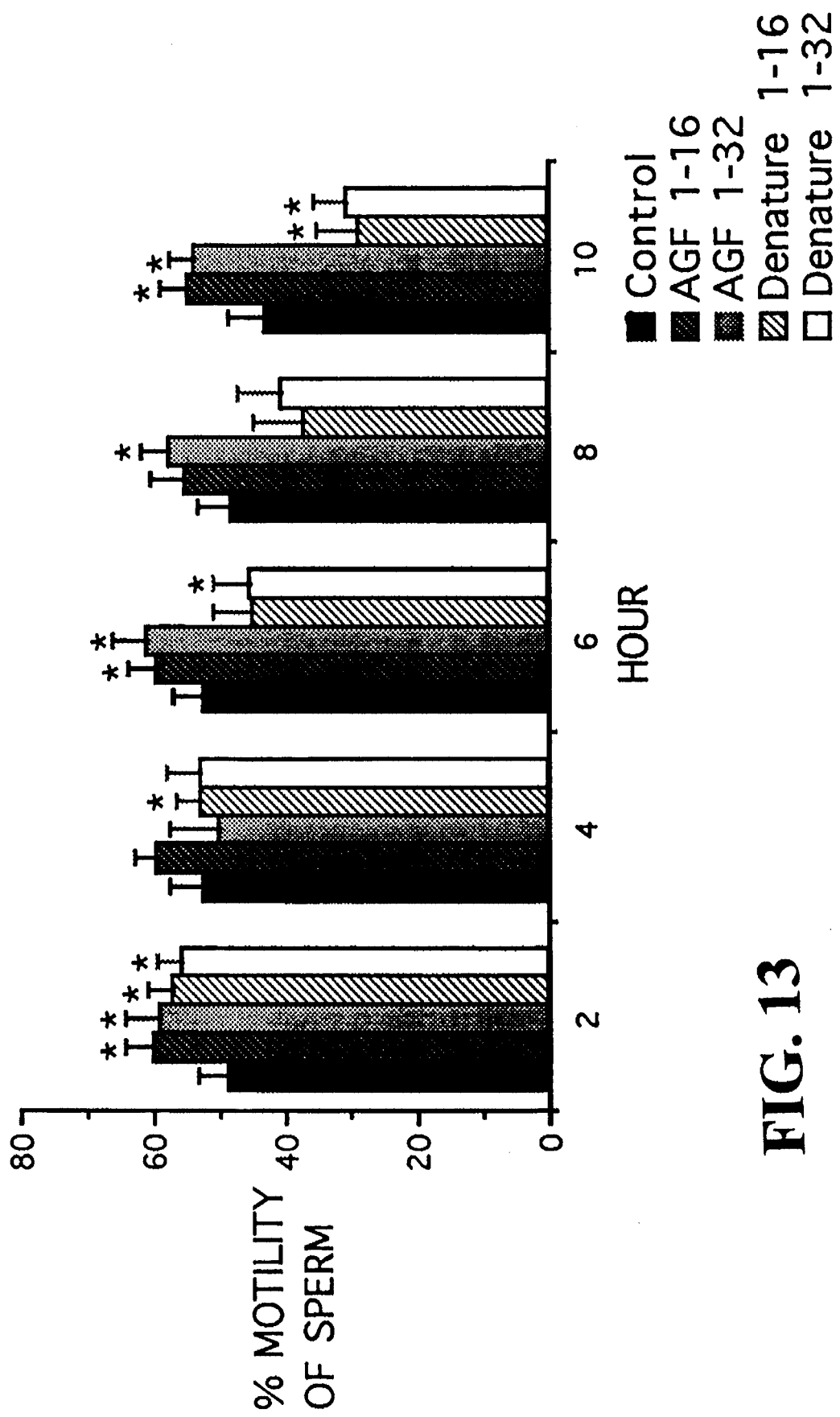
FIG. 13 is a bar graph demonstrating changes in the percent motility of human sperm after exposure to AGF and denatured AGF (1:16 and 1:32 dilutions). The asterisk (*) indicates a significant difference from control conditions (sperm exposed to washing medium only) at the same time interval (n=10 human subjects, Means ±SE, p>0.05).

Determination of the dilution factor of AGF to be used with human sperm was primarily based on the bihourly percent motility of sperm. Dilutions 1:16 and 1:32 sustained sperm motility for up to 10 hours, displaying moderate increases in percent motility in 4–6 hours (FIG. 13). Lower dilutions resulted in a steady decline in percent motility, just above the percent motility obtained under control conditions (HTF medium modified with 5 mg human albumin/ml).

Based on the above results, the effects of AGF dilutions 1:8 and 1:16 were investigated using human sperm. Washed human sperm samples were exposed to the following three treatments: 1) AGF, 2) heat denatured AGF, and 3) sperm washing medium. Heat denatured AGF was boiled for 15 minutes, and allowed to cool before dilution. An equal amount of washed sperm was then added to each treatment, yielding final dilutions of 1:16 and 1:32 of AGF and heat denatured AGF. Ten microliters of each treatment was assessed every two hours for ten hours using the Cell Soft Semen analyzer as described above.

Effects of AGF and Denatured AGF on normal sperm:

(1) % Motility.

The overall effect of AGF was to significantly increase the percent of motile human sperm (FIG. 13). Percent motility includes sperm within all of the WHO motility categories except non-motile. The maximum percent of motile sperm for AGF treatments was approximately 60%, for both dilution factors at hour 6. Comparisons made on hourly basis showed a significantly higher percent of motile sperm at hours 2, 6, and 10 in the presence of AGF at a dilution of 1:32, over those under control conditions (FIG. 13). The percent motility of sperm at hour 10 was about 25% higher than that under control conditions. The percent of motile sperm after exposure to AGF at a dilution of 1:16 were significantly higher at all hours except hour 4 when compared to control values (FIG. 13). The highest increase in the percent of motile sperm was 27% at hour 10. Hours 2, 6, and 8 were 22%, 14%, and 16% higher than control values, respectively.

Although the effects of denatured AGF were not significantly different from controls overall, the percent of motile sperm at hour 10 was significantly lower than that under control conditions (FIG. 13). Denatured AGF treatment at dilutions 1:16 and 1:32 were 34% and 29% lower than control values at hour 10, respectively. A significantly lower percent motility was noted between hours 6–10 when denatured AGF treatment (1:16 and 1:32) were compared with AGF treatments (FIG. 13). At hour 6, percent motility of sperm exposed to denatured AGF treatments was 24–26% lower than the percent motility observed after exposure to AGF. Upon completion of the study at hour 10, denatured AGF treatments were 43–58% lower than AGF treatments.

(2) Velocity.

Figure 14:
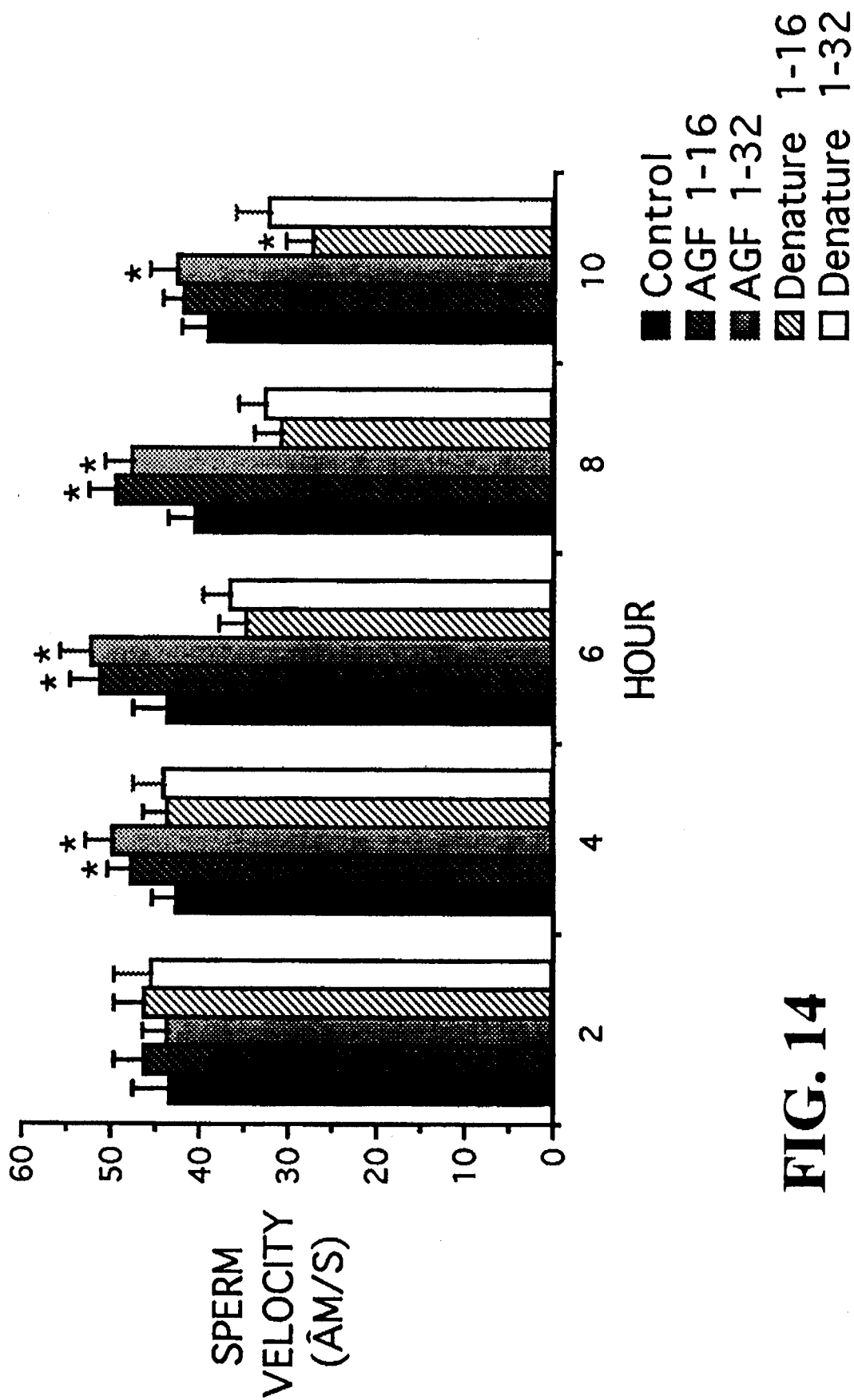
FIG. 14 is a bar graph demonstrating changes in the velocity of human sperm after exposure to AGF and denatured AGF (1:16 and 1:32 dilutions). Values are given as μm/sec. The asterisk (*) indicates a significant difference from control conditions (sperm exposed to washing medium only) at the same time interval (n=10 human subjects, Means ±SE, p>0.05).

Comparisons between sperm velocity among AGF, denatured AGF, and control treatments are shown in FIG. 14. The velocity of sperm exposed to AGF, regardless of dilution, was significantly higher at 2–8 hrs than control values. A peak velocity of 51 and 52 μm/s was noted at hour 6 in the presence of AGF at a dilution of 1:16 and 1:32, respectively. These rates were 18–20% higher than rates observed under control conditions and 30–32% higher than rates observed in denatured AGF treatments (FIG. 14). After 6 hours, the velocity slowly declined to a value not significantly different from control at hour 10 for sperm exposed to AGF at a 1:16 dilution. The velocity of sperm exposed to denatured AGF between hours 2–8 were not significantly different from that of control conditions at each time period. However, at 4–8 hrs at a dilution of 1:16 and 1:32, the velocity of sperm exposed to AGF was significantly higher than sperm exposed to denatured AGF. Within hours 4–8, the velocity of sperm exposed to denatured AGF decreased 12% while AFG treated sperm increased 7% in 4 hours (hour 2–6). The reduction in velocity resulting from denatured AGF (1:16 and 1:32) was 35% and 25% lower, respectively, than sperm in AGF treatments at hour 10.

(3) Linearity

Figure 15:
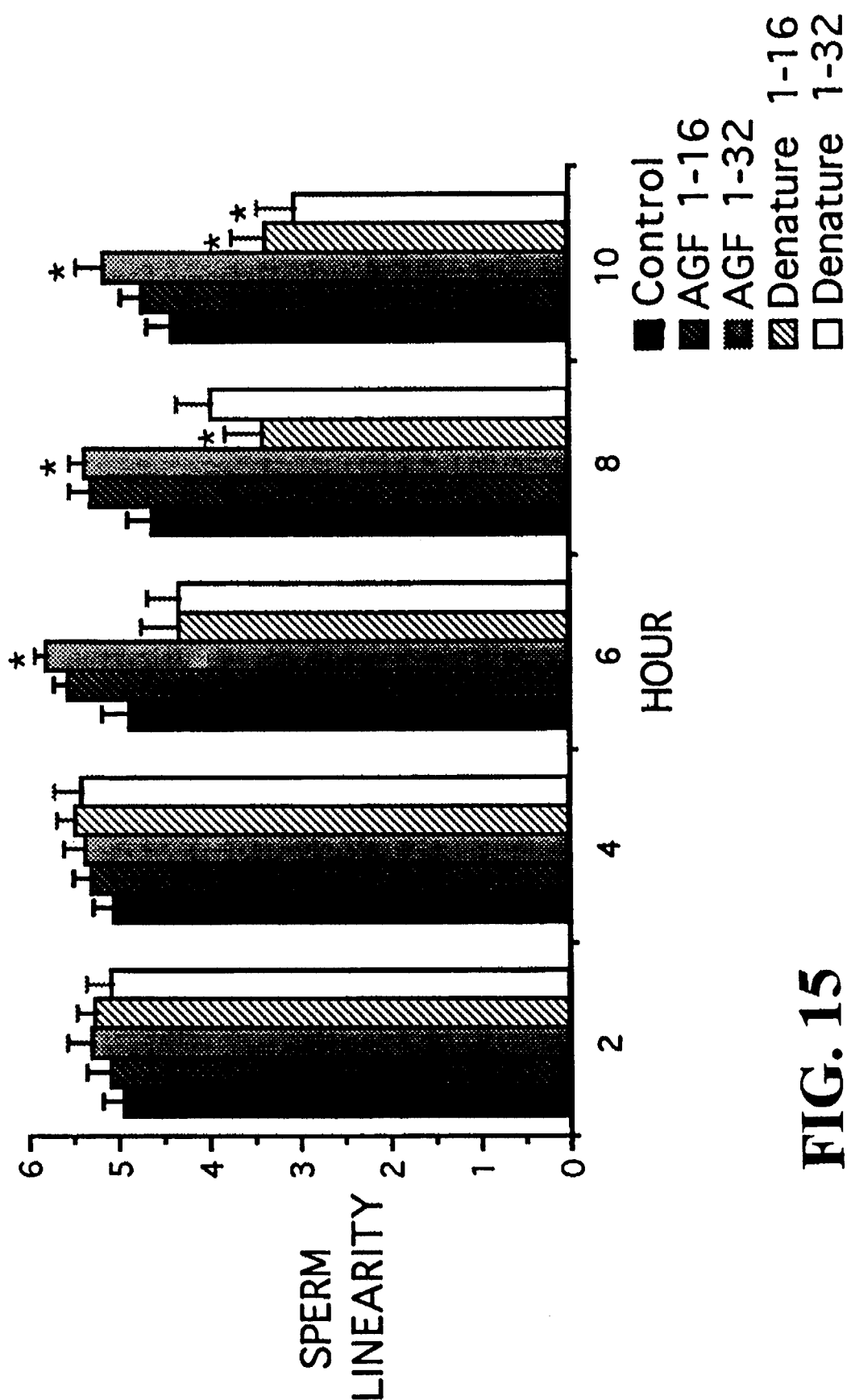
FIG. 15 is a bar graph demonstrating changes in the linearity of human sperm after exposure to AGF and denatured AGF (1:16 and 1:32 dilutions). The asterisk (*) indicates a significant difference from control conditions (sperm exposed to washing medium only) at the same time interval (n=10 human subjects, Means+SE, p>0.05).

Linearity of sperm movement was significantly higher with exposure to AGF at a 1:32 dilution than controls or denatured AGF treatments within 6–8 hours (FIG. 15). At a dilution of 1:16, AGF did not significantly alter sperm linearity when hourly comparisons were made with the control treatments. Hourly comparisons between AGF treatment and control and denatured AGF treatments at a 1:32 dilution show AGF exposure significantly increased the linearity of sperm at hours 6–10. Increases of 16–18% were observed over control values during this time period, whereas denatured AGF treatments (1:32) were 26% lower at hour 6 and 41% lower at hour 10, than AGF treatments (FIG. 15). Denatured AGF at a dilution of 1:16 was significantly lower at hours 8 and 10 by 26% and 24%, respectively, when compared to control conditions. At a dilution of 1:32, denatured AGF treatments were significantly lower than control by 15% and 31% for hours 8 and 10, respectively.

Effects of AGF on sperm from infertile men:

Tables 1–3 show the effect of AGF diluted 1:2, 1:4, 1:8 and 1:16 on sperm from infertile men. Table 1 shows that AGF diluted 1:2 with washing media significantly increased the percentage of motile sperm at both two and four hours after it was added. Longer time periods or greater dilutions had no significant effect on the percent motility. Likewise, AGF had no significant effect on velocity (Table 2) or linearity (Table 3) of sperm from these men.

TABLE 1

Percentage of motile spermatozoa (mean ± S.C.) from infertile men before and after treatment with different dilutions of AGF in vitro (n = 9).

| Hour of Incubation | Control | 1:2 | 1:4 | 1:8 | 1:16 |
|---|---|---|---|---|---|
| 2 hr | 37.9 ± 22.3 | 49.9 ± 22.4 | 42.5 ± 15.4 | 46.3 ± 17.5 | 37.9 ± 16.5 |
| p Value | — | 0.03 | N.S. | N.S. | N.S. |
| 4 hr | 39.1 ± 17.7 | 49.7 ± 22.3 | 45.8 ± 15.3 | 48.5 ± 21.5 | 44.6 ± 17.1 |
| p Value | — | 0.01 | N.S. | N.S. | N.S. |
| 6 hr | 38.8 ± 20.7 | 45.1 ± 21.5 | 40.3 ± 15.5 | 35.9 ± 15.5 | 32.1 ± 16.5 |
| p Value | — | N.S. | N.S. | N.S. | N.S. |
| 24 hr | 34.8 ± 18.4 | 33.9 ± 16.3 | 39.5 ± 16.7 | 42.2 ± 16.8 | 33.6 ± 13.3 |
| p Value | — | N.S. | N.S. | N.S. | N.S. |

TABLE 2

Velocity (μm/second) of motile spermatoza (mean ± S.D.) from infertile men before and after treatment with different dilutions of AGF in vitro (n = 9).

| Hour of Incubation | Control | 1:2 | 1:4 | 1:8 | 1:16 |
|---|---|---|---|---|---|
| 2 hr | 25.5 ± 5.3 | 27.8 ± 5.8 | 29.0 ± 5.3 | 33.6 ± 9.7 | 29.8 ± 5.0 |
| p Value | — | N.S. | N.S. | 0.05 | 0.06 |
| 4 hr | 28.8 ± 7.7 | 30.7 ± 8.1 | 29.6 ± 5.9 | 31.4 ± 8.0 | 30.2 ± 6.6 |
| p Value | — | N.S. | N.S. | N.S. | N.S. |
| 6 hr | 28.8 ± 3.6 | 33.2 ± 13.1 | 32.2 ± 7.4 | 29.0 ± 6.4 | 30.6 ± 5.4 |
| p Value | — | N.S. | N.S. | N.S. | N.S. |
| 24 hr | 28.3 ± 6.8 | 25.2 ± 6.2 | 29.5 ± 4.4 | 27.0 ± 5.1 | 27.9 ± 4.0 |

TABLE 2-continued

Velocity (μm/second) of motile spermatozoa (mean ± S.D.) from infertile men before and after treatment with different dilutions of AGF in vitro (n = 9).

| Hour of Incubation | Control | 1:2 | 1:4 | 1:8 | 1:16 |
|---|---|---|---|---|---|
| p Value | — | N.S. | N.S. | N.S. | N.S. |

TABLE 3

Linearity of motile spermatozoa (mean ± S.D.) from infertile men before and after treatment with different dilutions of AGF in vitro (n = 9).

| Hour of Incubation | Control | 1:2 | 1:4 | 1:8 | 1:16 |
|---|---|---|---|---|---|
| 2 hr | 3.4 ± 1.0 | 3.2 ± 0.9 | 3.9 ± 1.2 | 3.9 ± 1.6 | 3.7 ± 1.1 |
| p Value | — | N.S. | N.S. | N.S. | N.S. |
| 4 hr | 3.3 ± 0.9 | 3.7 ± 1.2 | 3.5 ± 1.1 | 3.6 ± 0.9 | 3.9 ± 1.0 |
| p Value | — | N.S. | N.S. | 0.02 | N.S.(0.07) |
| 6 hr | 3.9 ± 1.1 | 3.3 ± 0.9 | 3.6 ± 1.1 | 3.7 ± 1.1 | 3.6 ± 1.0 |
| p Value | — | N.S. | N.S. | N.S. | N.S. |
| 24 hr | 3.9 ± 1.0 | 3.8 ± 1.1 | 3.3 ± 1.4 | 3.0 ± 1.3 | 3.1 ± 1.0 |
| p Value | — | N.S. | N.S. | N.S. | N.S. |

Throughout this application various publications are referenced. The disclosures of these publications in their entireties are hereby incorporated by reference into this application in order to more fully describe the state of the art to which this invention pertains. The full citations for these publications are as follows:

REFERENCES

Barkay et al. The influence of in vitro caffeine treatment on human sperm morphology and fertilizing capacity. Fertil. Steril. 41:913–918, 1984.

Bedford, J. M. In Germ Cells and Fertilization, R. A. Austin and R. V. Short, eds. Cambridge: Cambridge University Press, 1982, p.128.

Borcea, I. Recherches sur la systeme urogenital des Elasmobranches. Arch. Zool. Exper. et gen. 4(4):199–484, 1906.

Daniels, F. J. Urogenital system. In The Elasmobranch Fishes, F. J. Daniels, ed. Berkeley, Calif. University of California, 1934, pp. 300–303.

DeJonge, C. J., S. R. Mack, and L. J. D. Zaneveld. Inhibition of the human sperm acrosome reaction by proteinase inhibitors. Gamete Res. 23:387–397, 1989.

DeJonge, D. J., S. M. Tarchala, R. G. Rawlins, Z. Binor, and E. Radwanska. Acrosin activity in human spermatozoa in relation to semen quality and in-vitro fertilization. Hum. Reprod. 8: 253–257, 1993.

Fénichel, P. Sperm engines—why don't we know more? Fertil. Steril. 59:243–244, 1993.

Fénichel, P. Proteins of movement. Fertil. Steril. 59:696, 1993.

Fishel, S. B. and J. Timson. In Infertility A. A., Templeton and J. O. Drife, eds. London: Springer-Verlag, 1992, pp. 115–132.

Harrison et al. Observations on the motility, ultrastructure and elemental compositions of human spermatozoa incubated with caffeine. Andrologia 12:434–443, 1980.

Hoshi, K., T. Sugano, C. Endo, N. Yoshimatsu, K. Yanagida, and A. Sato. Induction of the acrosome reaction in human spermatozoa by human zona pellucida and effect of cervical mucus on zona-induced acrosome reaction. Fertil. Steril. 60:149–153, 1993.

Koukoulis, G. N., D. Vantman, L. Dennison, S. M. Banks, and R. J. Sherins. Low acrosin activity in a group of men with idiopathic infertility does not correlate with sperm density, percent motility, curvilinear velocity, or linearity. Fertil. Steril. 52:120–127, 1989.

Lison, D., S. Tas, J. P. Gennart, I. Psalti, S. De Cooman, and R. Lauwerys. Plasminogen activator activity and fertilizing ability of human spermatozoa. Int. J. Androl. 16:201–206, 1993.

Mahadevan, M. M., and A. O. Trounson. The influence of seminal characteristics on the success rate of human in vitro fertilization. Fertil. Steril. 42:400, 1984.

Maren, T. H., J. A. Rawls, J. W. Burger, and A. C. Myers. The alkaline (Marshall's) gland of the skate. Comp. Biochem. Physiol. 10:1–16, 1963.

Masur, S. K. Electrol microscopy of the alkaline gland epithelium of the little skate, Raja erinacea. Bull. Mt. Desert Is. Biol. Lab. 24:96–97, 1984.

Pang, S. C., D. B. Williams, T. Huang, and C. Wang. Effects of pentoxifylline on sperm motility and hyperactivated motility in vitro: a preliminary report. Fertil. Steril. 59:465–467, 1993.

Psalti, I. K. Thomas, and S. De Cooman. Effects of hyaluronate, strontium and prolonged incubation on different sperm parameters. Gynecol. Obstet. Invest. 36:47–51, 1993.

Rees, J. M., W. C. L. Ford, and M. G. R. Hull. Effect of caffeine and of pentoxifylline on the motility and metabolism of human spermatozoa. J. Reprod. Fert. 90:147–156, 1990.

Shen, M.-R., Ph.-H. Chiang, R.-C. Yang, C.-Y. Hong, and S.-S. Chen. Pentoxifylline stimulates human sperm motility both in vitro and after oral therapy. Br. J. Clin. Pharmac. 31:711–714, 1991.

Sikka, S. C., and W. J. G. Hellstrom. The application of pentoxifylline in the stimulation of sperm motion in men undergoing electroejaculation. *J. Androl.* 12:165–170, 1991.

Smith, H. W. The composition of the body fluids of elasmobranchs. *J. Biol. Chem.* 81:407–419, 1929.

Smith, P. L. Electrolyte transport by the alkaline gland of the little skate, Rata erinacea. Mechanism of luminal alkalinization. *Bull. Mt. Desert Is. Biol. Lab.* 21:80–83, 1981.

Smith, P. L. Electrolyte transport by alkaline gland of little skate Rata erinacea. *Am. J. Physiol.* 248:346–352, 1985.

Tesarik, J., and C. Mendoza. Sperm treatment with pentoxifylline improves the fertilizing ability in patients with acrosome reaction insufficiency. *Fertil. Steril.* 60:141–148, 1993.

Tesarik, J., A. Thébault, and J. Tesart. Effect of pentoxifylline on sperm movement characteristics in normozoospermic and asthenozoospermic specimens. *Hum. Reprod.* 7:1257–1263, 1992.

Tournaye, H., R. Janssens, M. Camus, C. Staessen, P. Devroey, and A. van Steirteghem. Pentoxifylline is not useful in enhancing sperm function in cases with previous in vitro fertilization failure. *Fertil. Steril.* 59:210–215, 1993.

Tucker, M. J., and S. Y. W. Chan. Origins and effects of variations in spermatozoal quality. *Int. J. Fertil,* 38:197–2009, 1993.

Winston, R. M. L., and A. H. Handyside. New challenges in human in vitro fertilization. *Science* 260:932–936, 1993.

Yovich, J. M., W. R. Edirisinghe, J. M. Cummins, and J. L. Yovich. Preliminary results using pentoxifylline in a pronuclear stage tubal transfer (PROST) program for severe male factor infertility. *Fertil. Steril.* 50:179–183, 1988.

Yovich, J. M., W. R. Edirisinghe, J. M. Cummins, and J. L. Yovich. Influence of pentoxifylline in severe male factor infertility. *Fertil Steril.* 53:715–722, 1990.

What is claimed is:

1. A purified protein of approximately 14 kD, determined by sodium dodecyl sulfate polyacrylamide gel electrophoresis under non-denaturing conditions, that decreases sperm motility in vitro and can be purified from the alkaline gland of a stingray.

2. A composition comprising the protein of claim 1 and a pharmaceutically acceptable carrier.

3. The composition of claim 2, further comprising a spermicide.

4. A purified protein of approximately 350 kD, determined by sodium dodecyl sulfate polyacrylamide gel electrophoresis under non-denaturing conditions, that increases sperm motility in vitro and can be purified from the alkaline gland of a stingray.

5. A method of increasing sperm motility comprising contacting the sperm in vitro with an amount of the protein of claim 4 effective to increase the motility of the sperm in vitro.

6. A purified protein of approximately 40 kD, determined by sodium dodecyl sulfate polyacrylamide gel electrophoresis under non-denaturing conditions, that increases sperm motility in vitro and can be purified from the alkaline gland of a stingray.

7. A method of increasing sperm motility comprising contacting the sperm in vitro with an amount of the protein of claim 6 effective to increase the motility of the sperm in vitro.

8. A purified protein of approximately 22 kD, determined by sodium dodecyl sulfate polyacrylamide gel electrophoresis under non-denaturing conditions, that increases sperm motility in vitro and can be purified from the alkaline gland of a stingray.

9. A method of increasing sperm motility comprising contacting the sperm in vitro with an amount of the protein of claim 8 effective to increase the motility of the sperm in vitro.

10. A method of increasing sperm motility comprising contacting the sperm in vitro with an amount of a composition comprising purified alkaline gland fluid from the alkaline gland of a stingray effective to increase the in vitro motility of the sperm.

* * * * *